United States Patent [19]
Haemmerle et al.

[11] Patent Number: 5,858,658
[45] Date of Patent: Jan. 12, 1999

[54] METHOD OF QUANTITATING GENOMIC DNA

[75] Inventors: Thomas Haemmerle; Falko-Guenter Falkner, both of Orth/Donau; Johann Kohl, Vienna; Michele Himmelspach, Vienna; Friedrich Dorner, Vienna, all of Austria

[73] Assignee: Immuno Aktiengesellschaft, Vienna, Austria

[21] Appl. No.: 533,967

[22] Filed: Sep. 26, 1995

[30] Foreign Application Priority Data

Sep. 26, 1994 [AT] Austria .................................. 1830/94

[51] Int. Cl.⁶ ............................... C12Q 1/68; C12Q 1/70
[52] U.S. Cl. ...................................... 435/6; 435/5
[58] Field of Search .................. 435/5, 6, 91.2; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 5,213,961 | 5/1993 | Bunn | 435/6 |
| 5,457,027 | 10/1995 | Nadeau | 435/6 |

FOREIGN PATENT DOCUMENTS

| | | |
|---|---|---|
| 0 594 959 | 6/1994 | European Pat. Off. . |
| 92/13101 | 8/1992 | WIPO . |
| 93/23573 | 11/1993 | WIPO . |
| 94/04706 | 3/1994 | WIPO . |
| 94/12669 | 6/1994 | WIPO . |

OTHER PUBLICATIONS

Derwent Publications Ltd., London, GB; AN 86–234649 XP002022980 "Detection of dna and/or rna involves hybridising single stranded dan and/or rna labelled probe comprising repetitive sequence in dna and/or rna and detecting label," & JP–A–61 162 752 (Sekisui Chem Ind KK) 23 Jul. 1986.

Diviacco, "A novel procedure for quantitative polymerase chain reaction by coamplification of of competitive templates", Gene, vol. 122, No. 2, (1992) pp. 313–320.

Batzer et al., "Structure and Variability of Recently Inserted Alu Family Members", Nucleic Acids Research, vol. 18, No. 23 (1990), pp. 6793–6798.

Stumph et al., "Genomic Structure and Possible Retroviral Origin of the Chicken CRI Repetitive DNA Sequence Family", Proc. Natl. Acad. Sci. USA, vol. 81, (1984), pp. 6667–6671.

Saiki et al., "Primer–Directed Enzymatic Amplification of DNA With a Thermostable DNA Polymerase", Reports, vol. 239, (1988), pp. 487–491.

Mullis et al., "Specific Synthesis of DNA in Virto Via a Polymerase–Catalyzed Chain Reaction", Methods in Enzymology, vol. 155, (1987), p. 351.

Jelinek et al., "Repetitive Sequences in Eukaryotic DNA and Their Expression", Ann. Rev. Biochem. (1982), pp. 814–843.

Barrett et al., "Large–Scale Production and Purification of Vaccinia Recombinant–Derived HIV–1 gp 160 and Analysis of Its Immunogenicity", Aids Research and Human Retroviruses, vol. 5, No. 2, (1989), pp. 159–171.

Stumph et al., "A Chicken Middle–Repetitive DNA Sequence Which Shares Homology With Mammalian Ubiquitous Repeats", Nucleic Acids Res., vol. 9, No. 20, (1981), pp. 5383–5397.

Per et al., "Quantification of Residual DNA in Biological Products", Clinical Chemistry, vol. 35, No. 9, (1989), pp. 1859–1860.

Robertson et al., "A Collaborative Study to Examine the Sensitivity and Reproducibility of Assays for the Detection of DNA in Biologicals Derived From Continuous Cell Lines", Biologicals, vol. 20, (1992), pp. 73–81.

Gilliland et al., "Analysis of Cytokine mRNA and DNA: Detection and Quantitation by Competitive Polymerase Chain Reaction", Proc. Natl. Acad. Sci., vol. 87, (1990), pp. 2725–2729.

Wang et al., "Quantitation of mRNA by the Polymerase Chain Reaction", Proc. Natl. Acad. Sci., vol. 86. (1989), pp. 9717–9721.

Porcher et al., "A Simplified Method for Determination of Specific DNA or RNA Copy Number Using Quantitative PCR and an Automatic DNA Sequencer", Resch. Report, vol. 13, No. 1, (1992), pp. 106–113.

Primary Examiner—Eggerton A. Campbell
Attorney, Agent, or Firm—Foley & Lardner

[57] ABSTRACT

A method of quantitating genomic DNA in a sample is provided. The method comprises the steps of adding to the sample a given amount of at least one nucleic acid as an internal standard, wherein the standard nucleic acid differs from the genomic DNA to be quantified in at least one detectable characteristic; amplifying the genomic DNA and the internal standard nucleic acid by means of a nucleic acid amplification process employing primers complementary to repetitive genomic sequences; determining as a first amount the amount of amplified genomic DNA, and determining as a second amount the amount of amplified standard nucleic acid; and determining from the first and second amounts, as a third amount, the amount of genomic DNA originally contained in the sample. Kits for performing the method and products substantially free of foreign DNA as determined by the method also are provided.

23 Claims, 16 Drawing Sheets

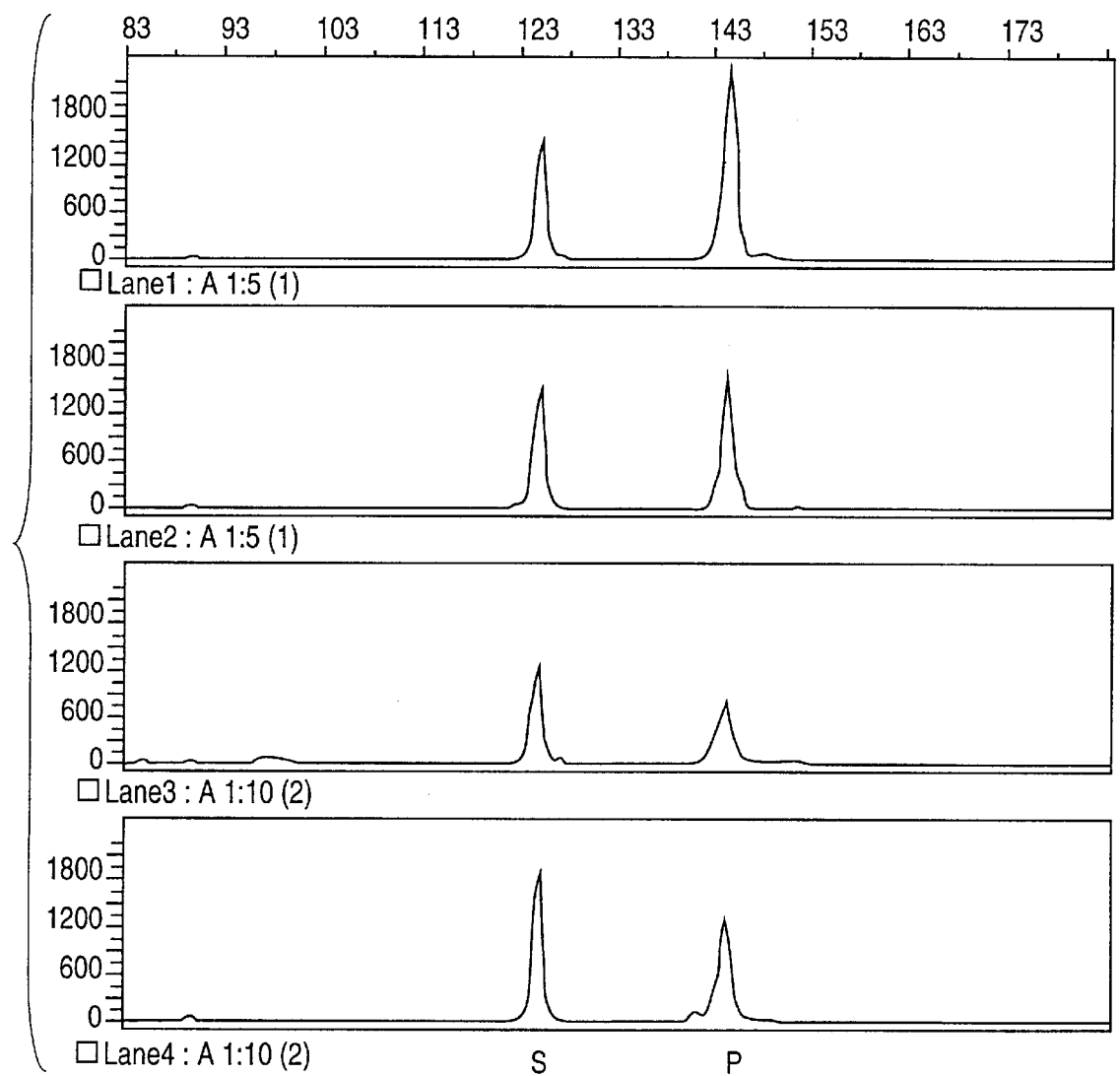
FIG. 2-A

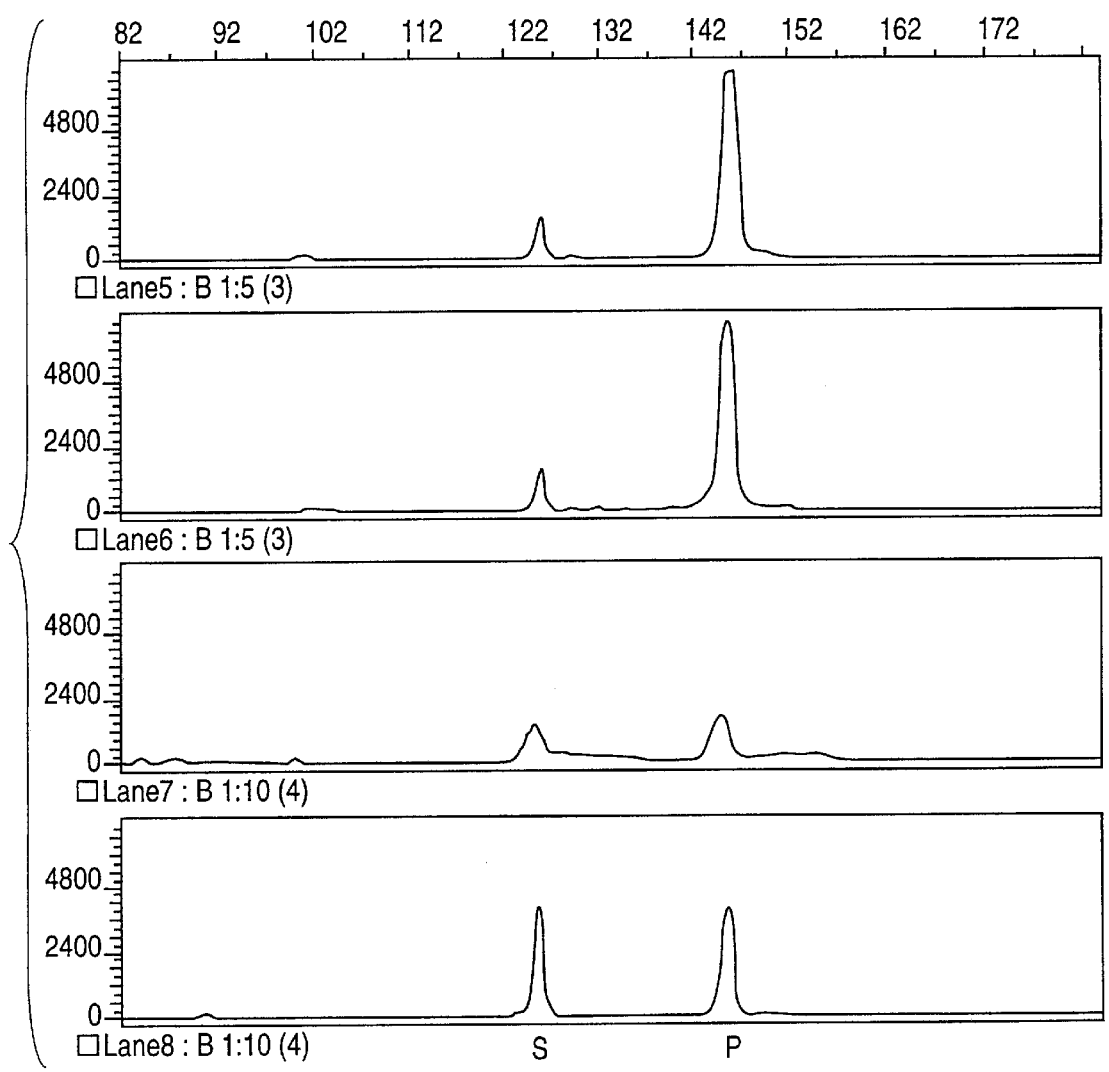

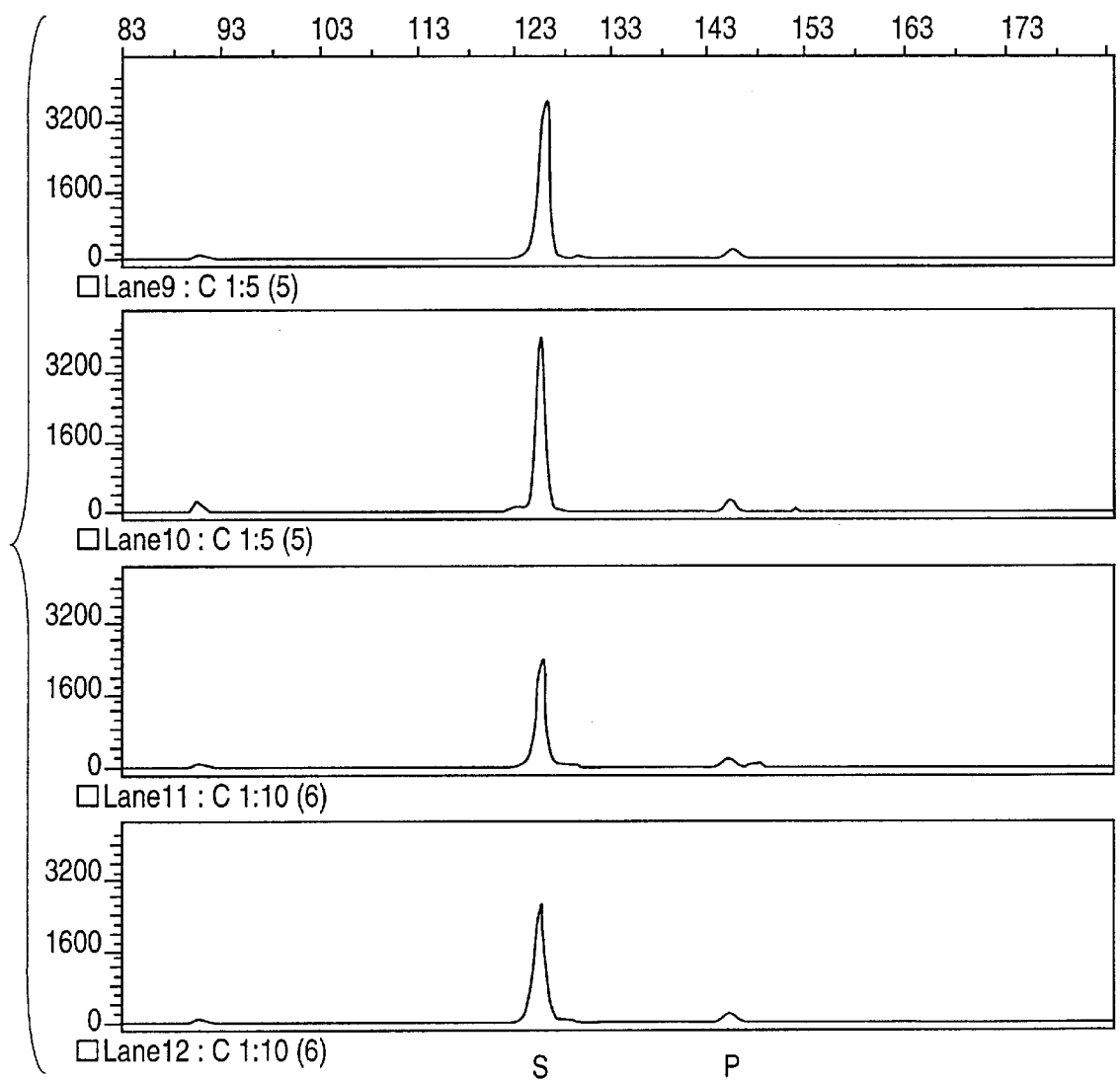
FIG. 2-C

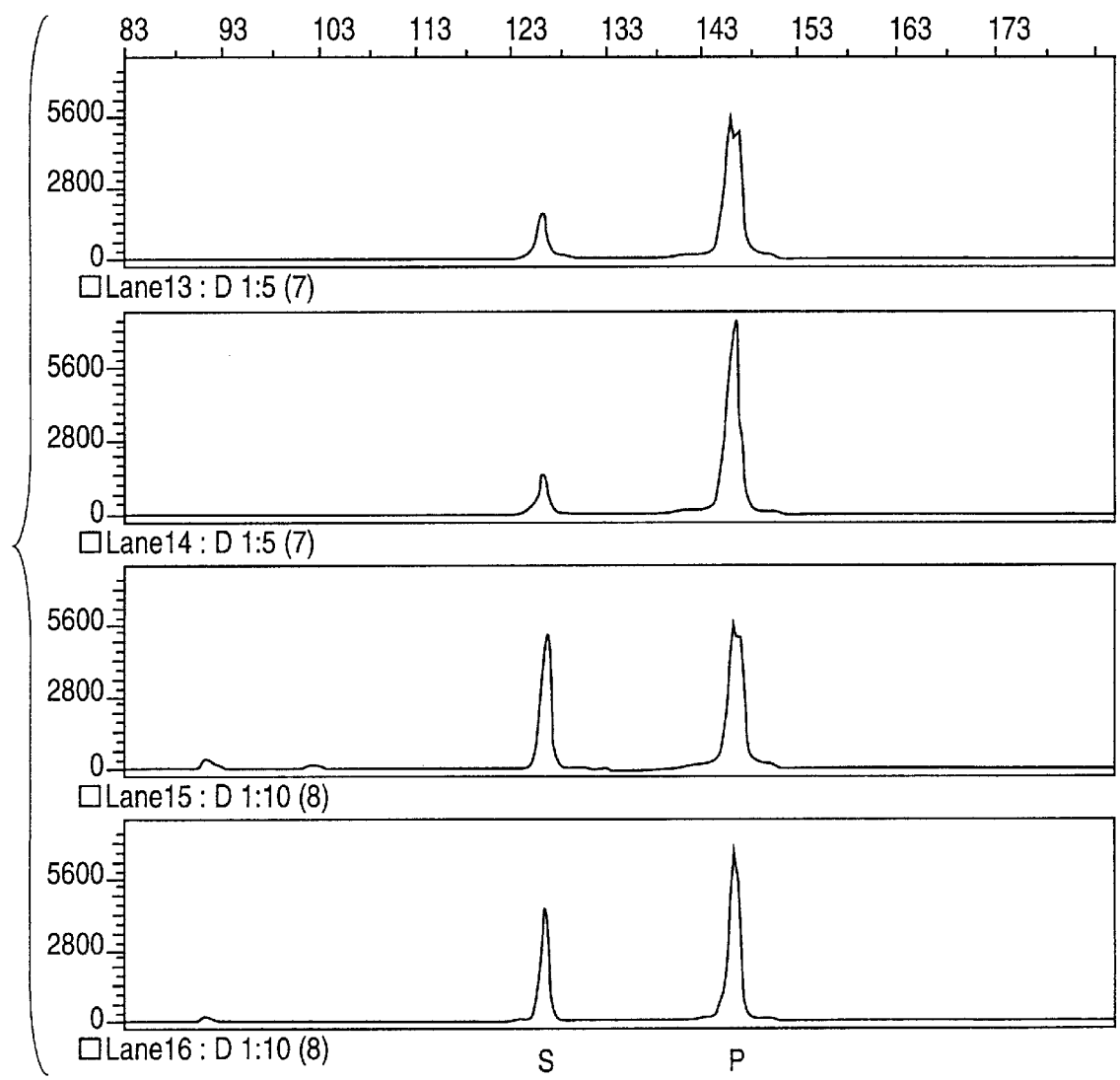
FIG. 2-D

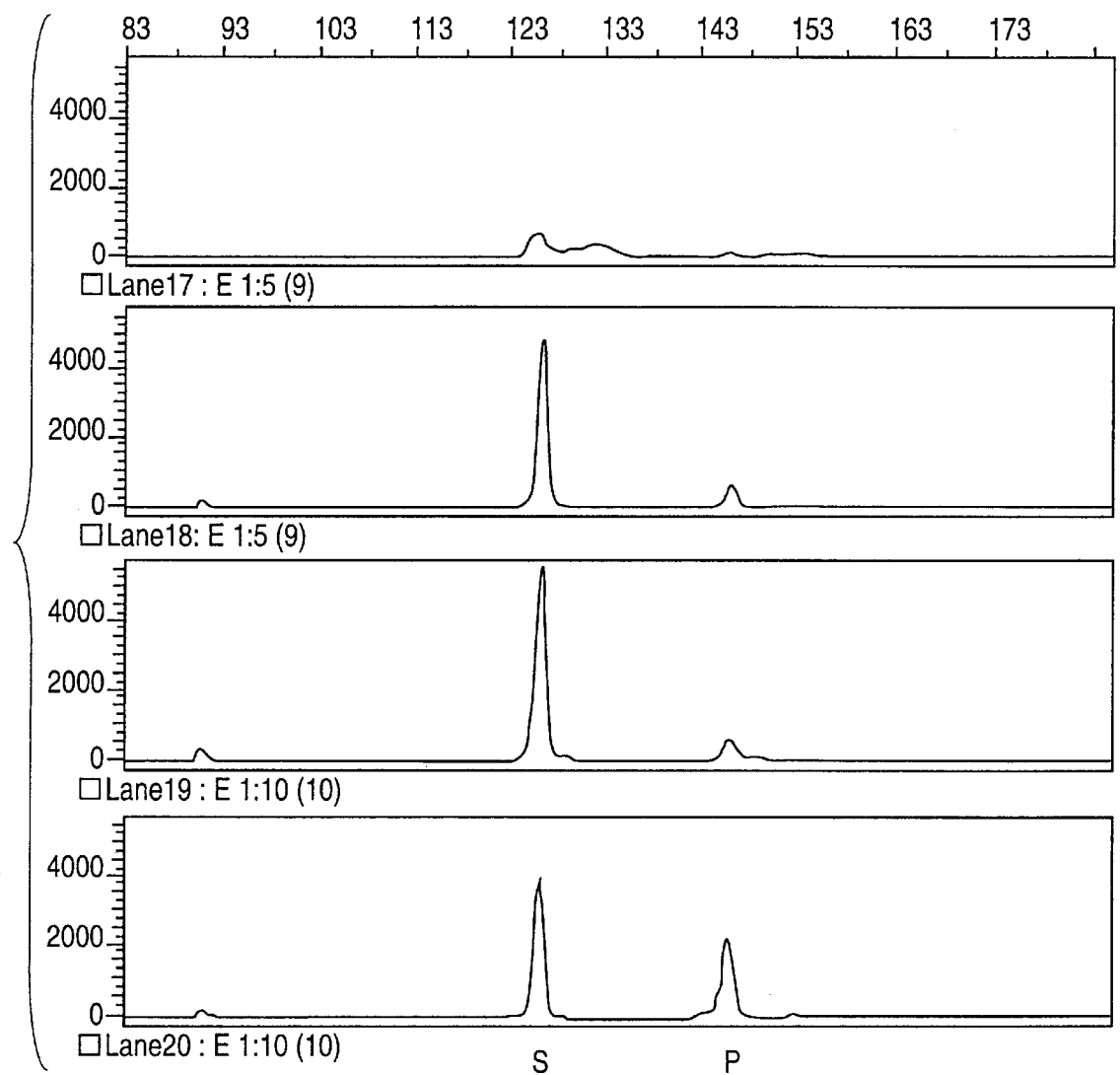
FIG. 2-E

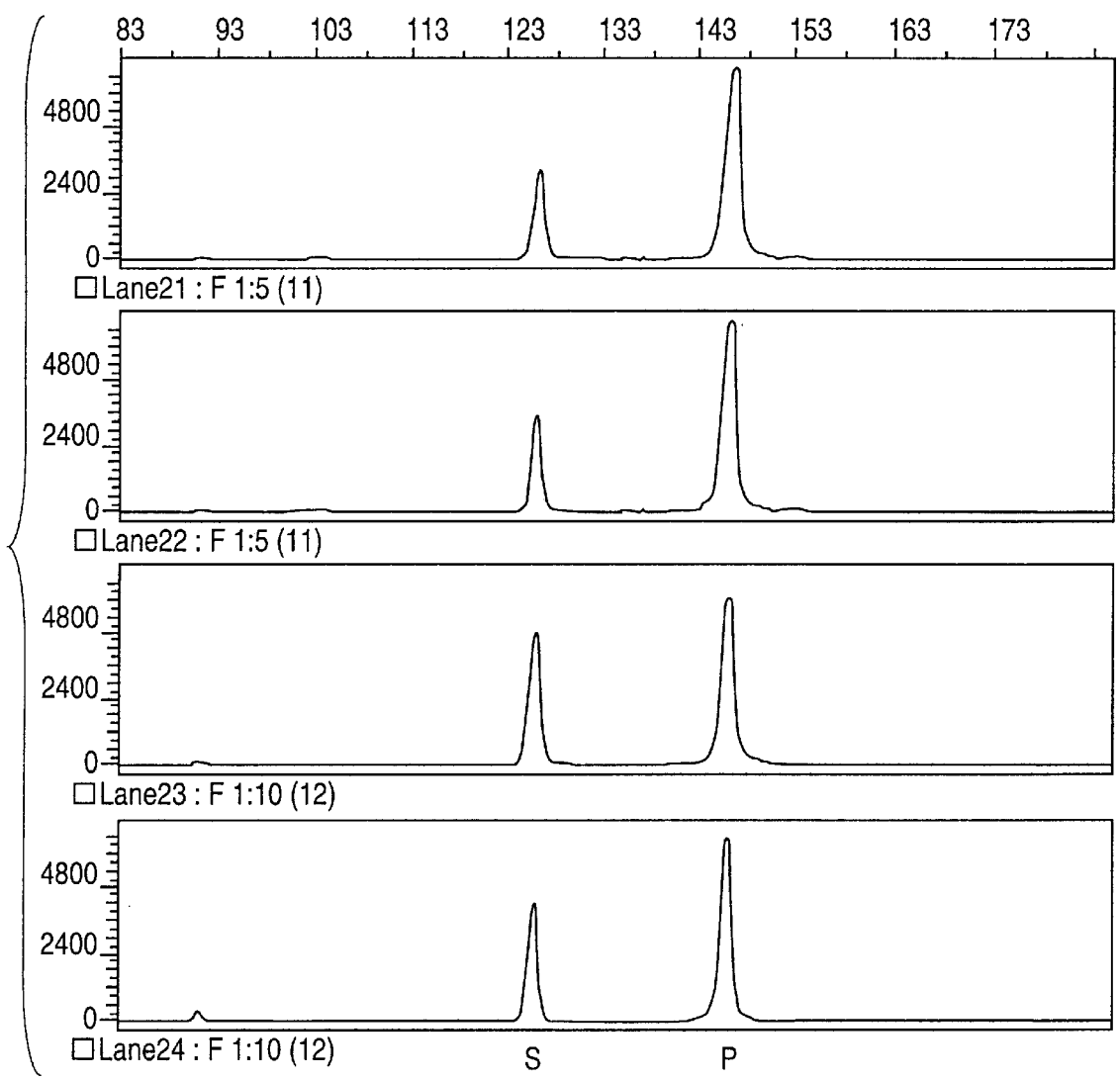
FIG. 2-F

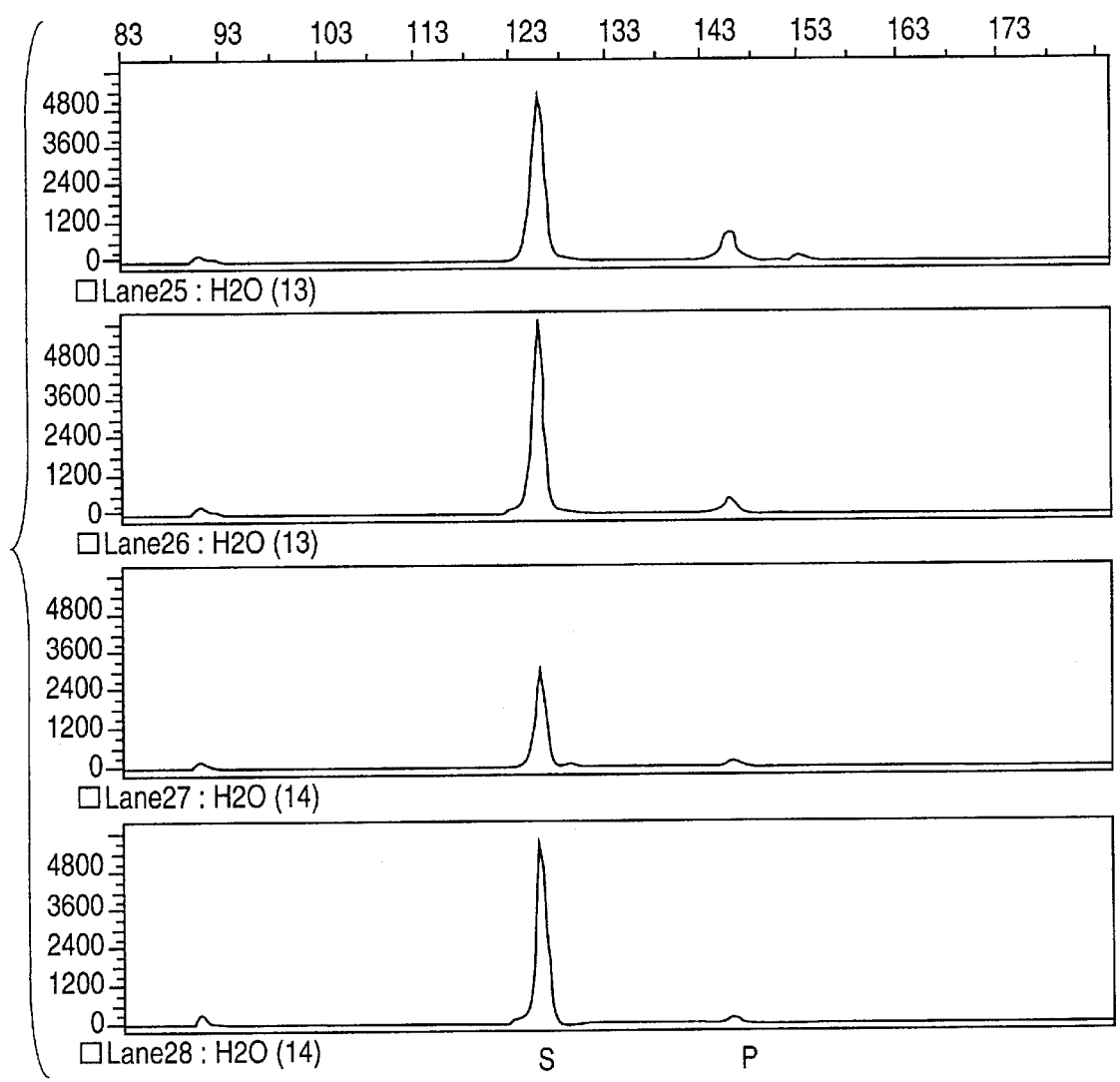
FIG. 2-G

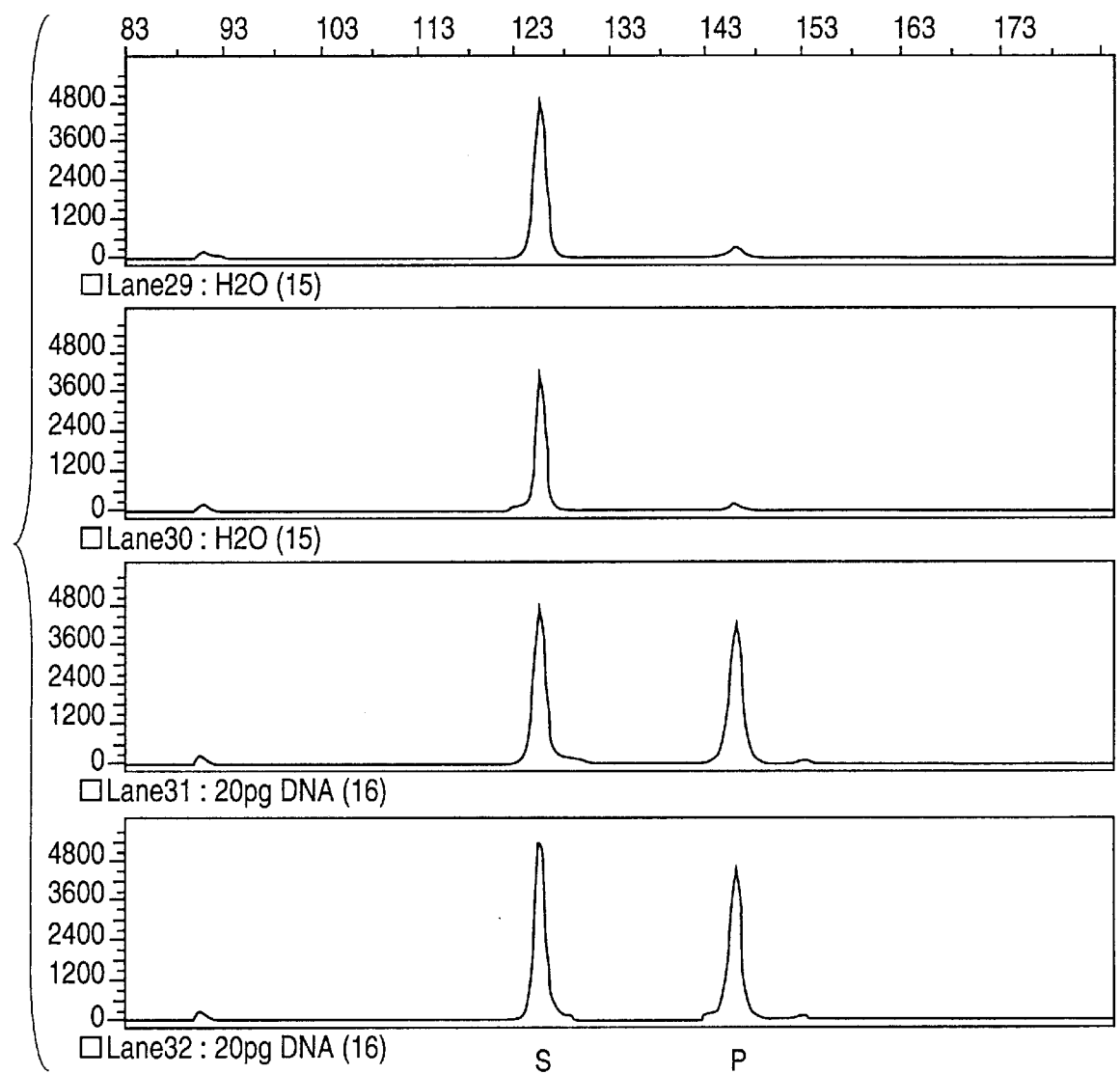
FIG. 2-H

FIG. 2-I
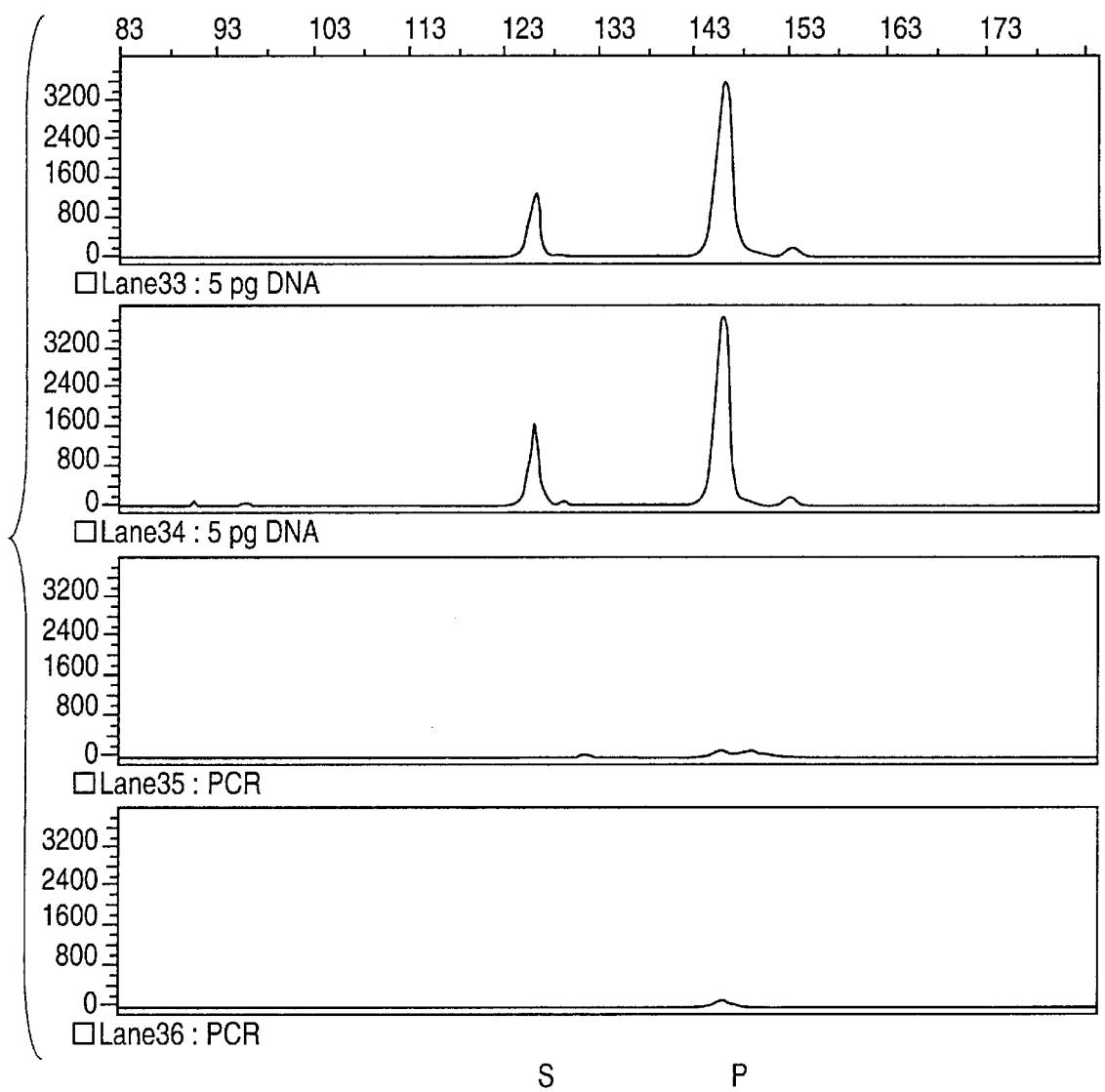

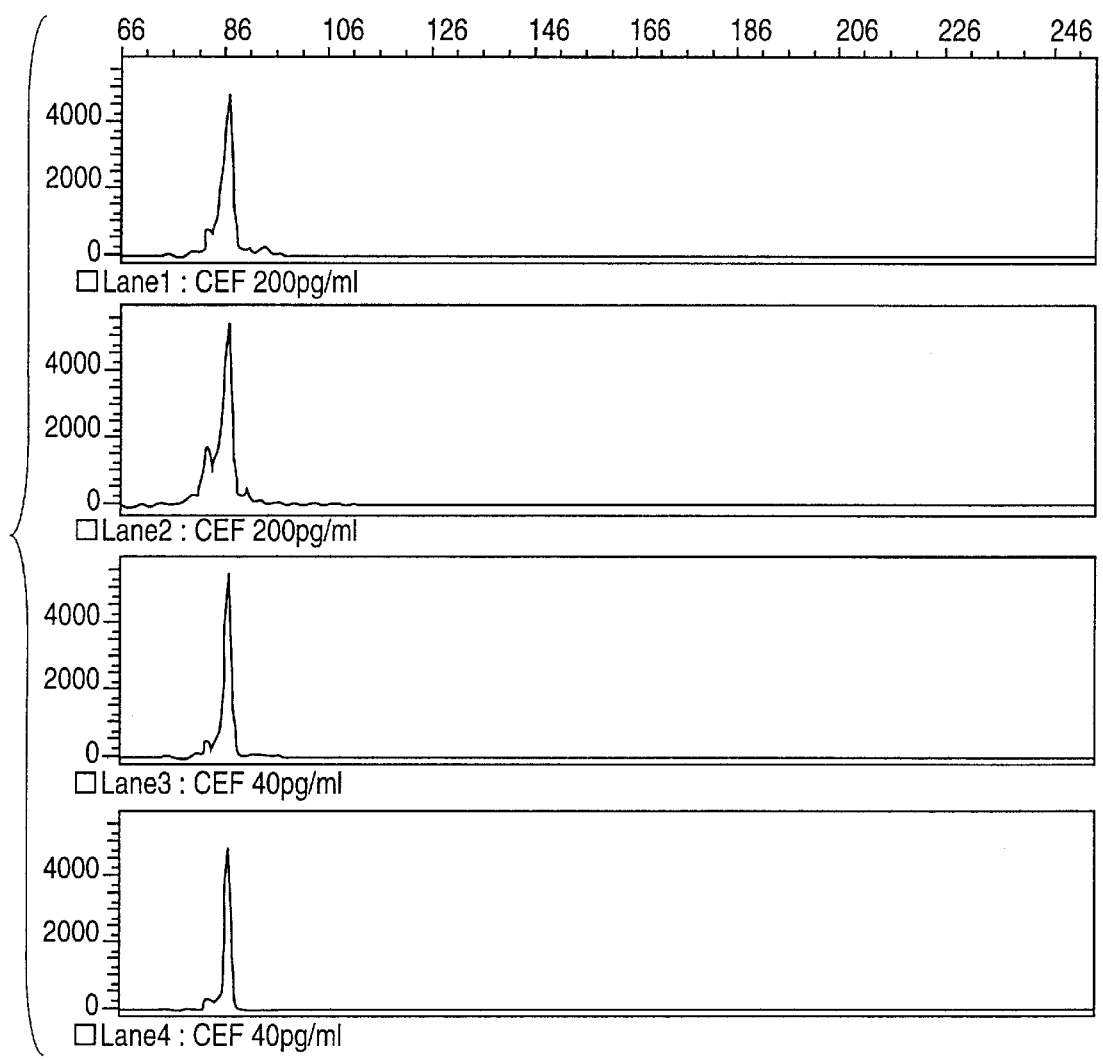
FIG. 3-A

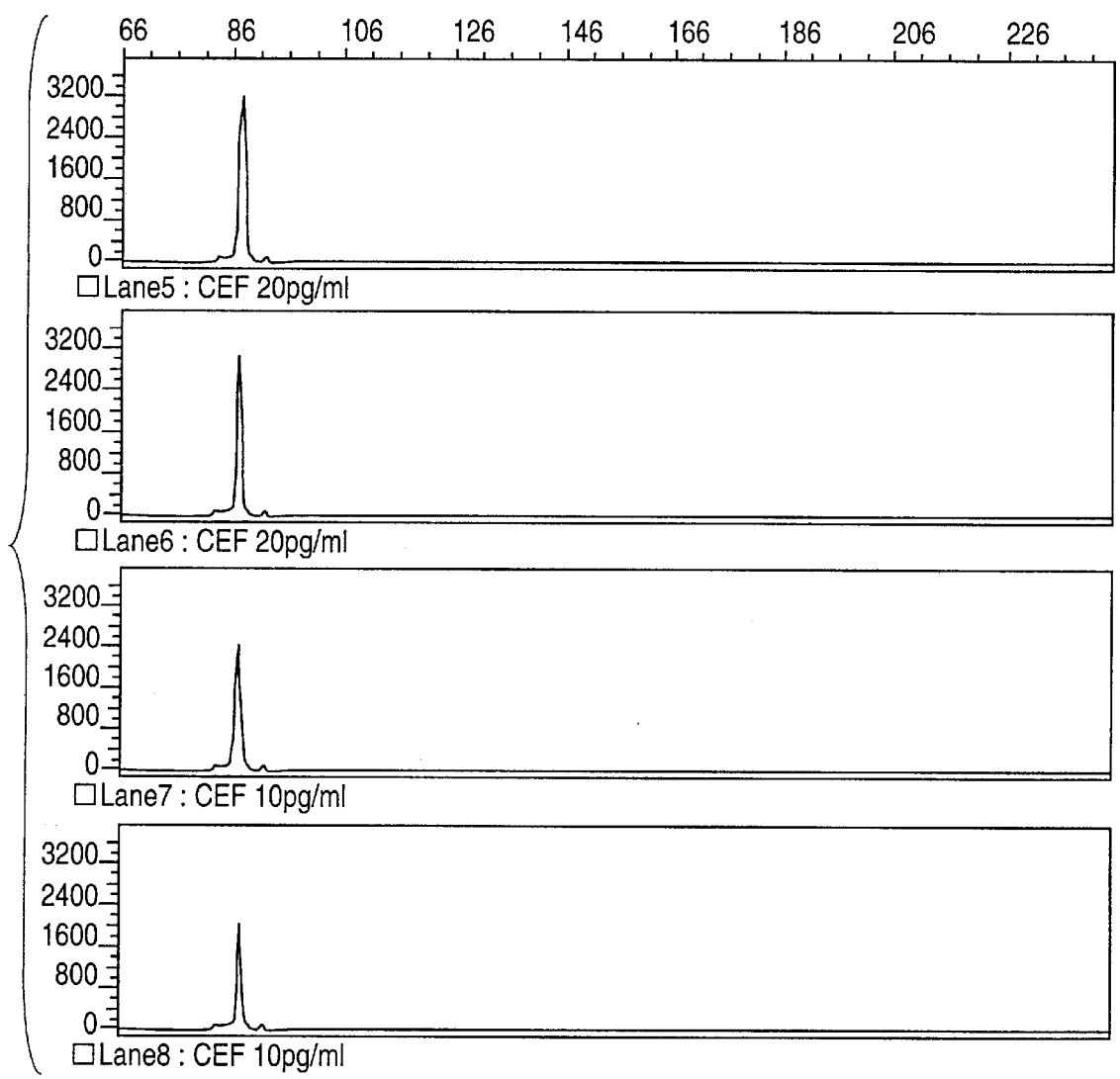
FIG. 3-B

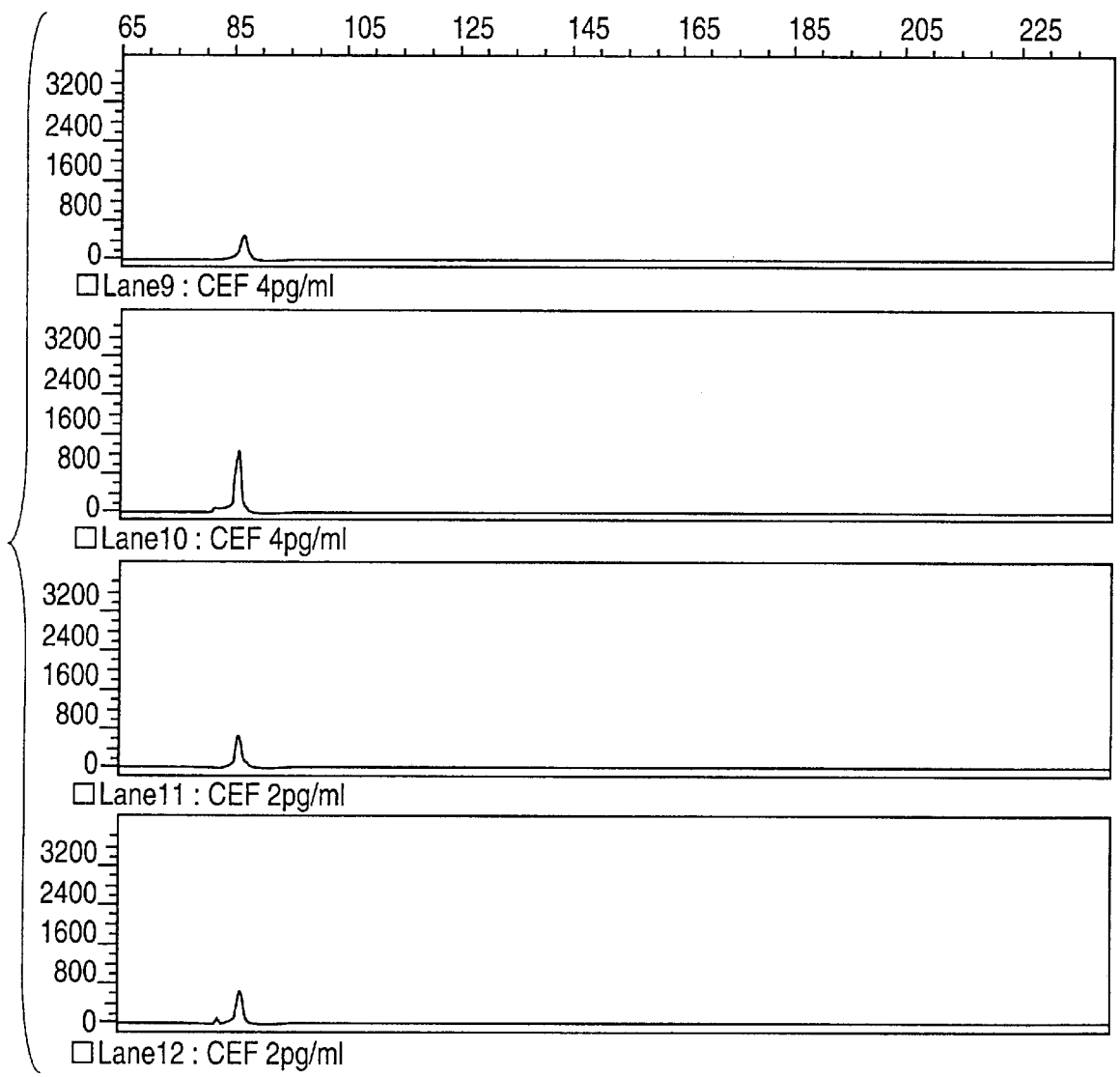
FIG. 3-C

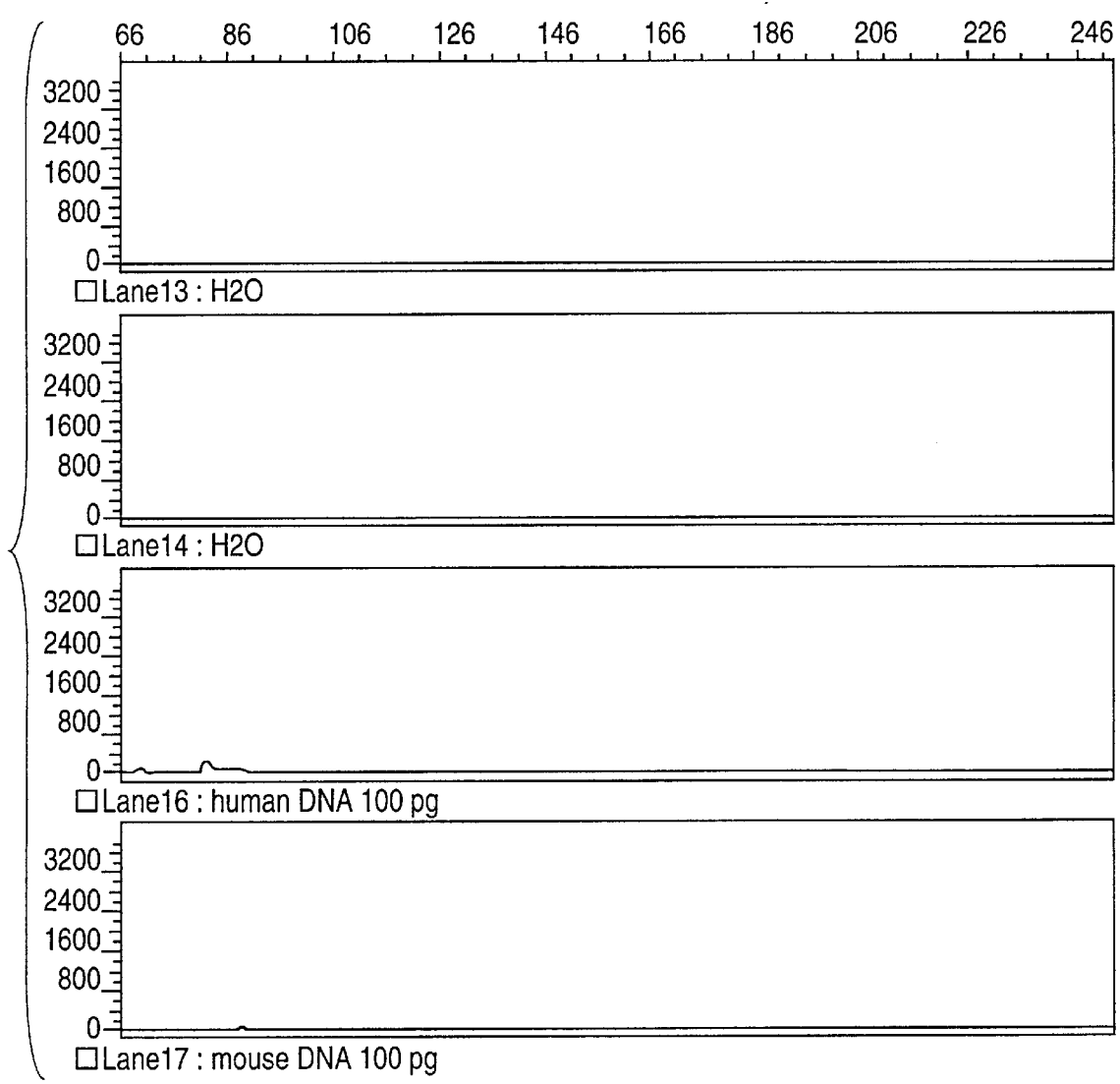
FIG. 3-D

FIG. 3-E
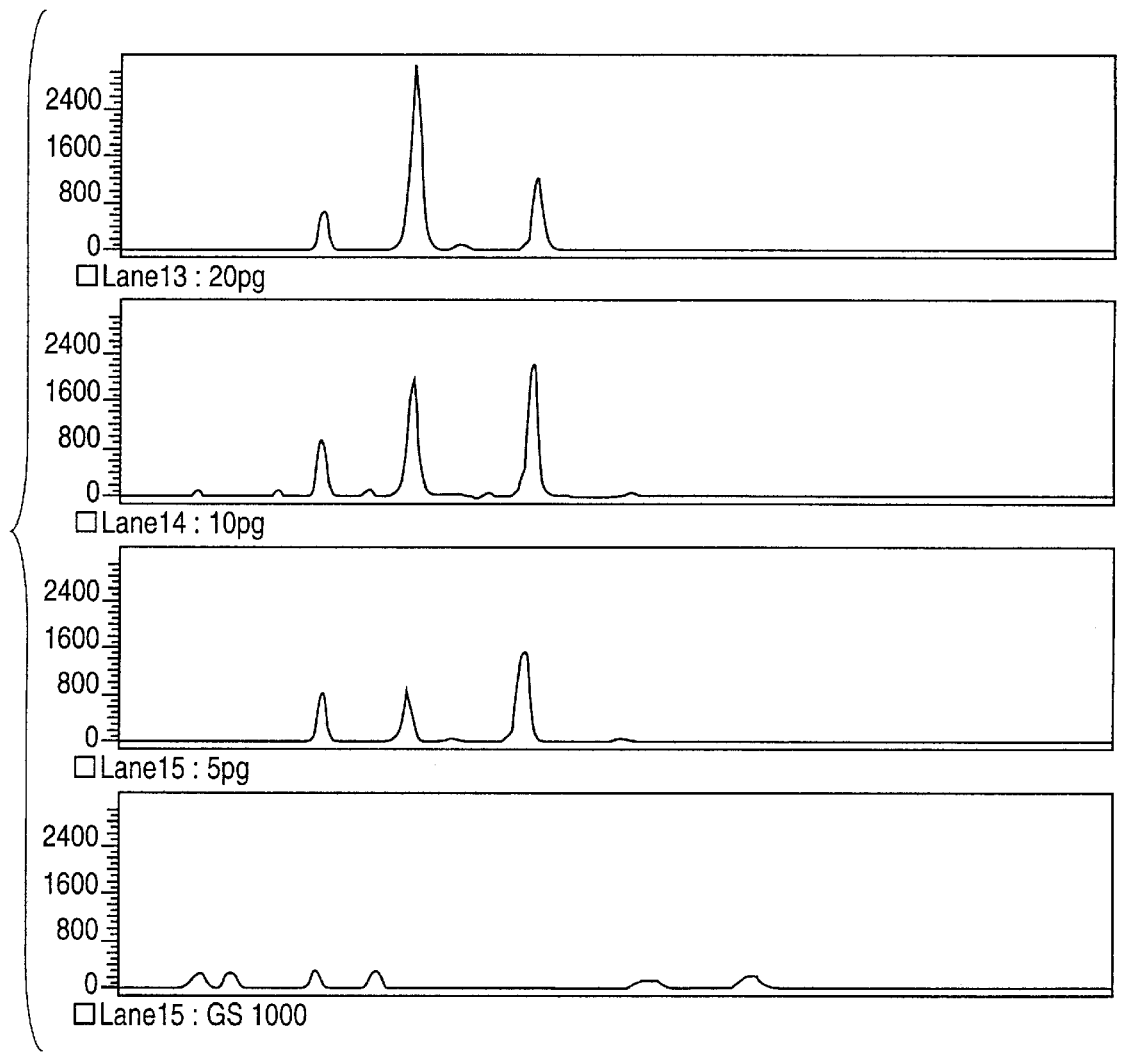

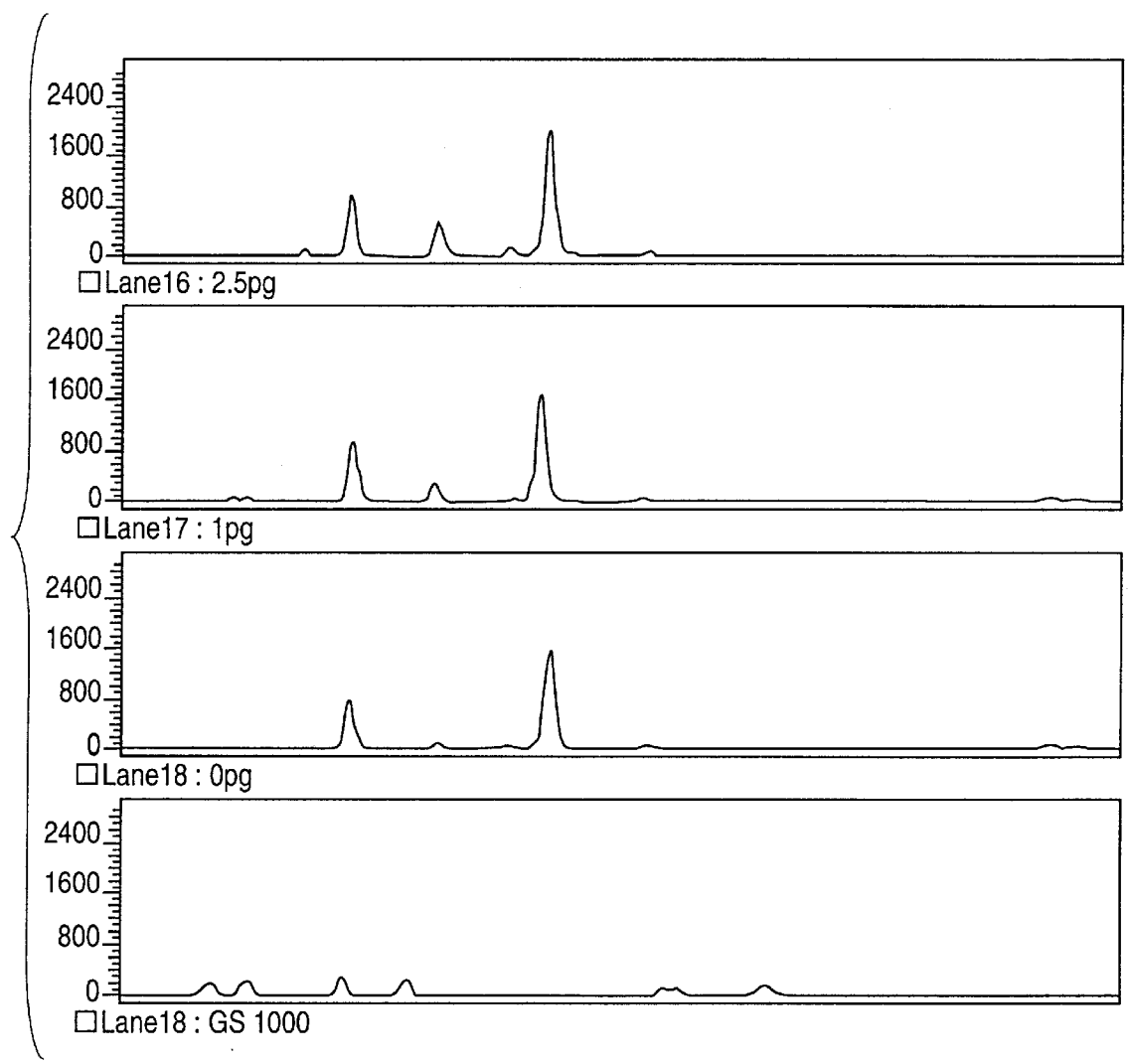
FIG. 3-F

METHOD OF QUANTITATING GENOMIC DNA

The invention relates to a method of quantitating genomic DNA in a sample comprising the steps of
  amplifying the DNA contained in the sample by a nucleic acid amplification process by using primers that are complementary to repetitive genomic sequences, and detecting the amplified DNA obtained.

In the medical field, the use of biotechnologically recovered proteins poses new problems for the pharmaceutical industry as regards quality control of their products. New detection methods must be established to determine impurities derived from the cell culture. Thus, e.g., the World Health Organization demands that the amount of heterologous contaminating DNA in recombinant products be below 100 pg per administered dose, whereas according to the requirements of the U.S. Food and Drug Administration only 10 pg of DNA per individual dose are accepted.

Hitherto, the determination of contaminating DNA in recombinant products has been mainly effected by hybridizing on membranes. Per (Clin. Chem. 35 (1989), 1859) shows that as low as 5 pg of DNA can be detected, if radioactively labelled genomic probes are used. An interlaboratory test, in which fourteen laboratories participated, has, however, shown that the DNA determination by hybridizing does not yield satisfying reproducible results, neither within one laboratory, nor when comparing several laboratories (Robertson and Heath, Biologicals 20 (1992), 73).

Gilliland describes a quantitative PCR method based on a competitive PCR (PNAS 87 (1990), 2725). To determine DNA amounts, he uses a dilution series of the internal standard which is amplified simultaneously with the sample. The PCR is carried out until saturation. This also allows for the detection of the PCR products by means of ethidium bromide staining. Subsequently, the PCR products are separated on a gel, the number of copies of the sample is compared to the number of copies of the standard dilution series, and thus the concentration of the sample is estimated. This concentration estimate will be exact if the concentration of the standard and the sample have been amplified in a reaction vessel approximately at a ratio of 1:1. This, in turn, implies that the determination of the DNA amount will be the more precise, the more standard dilutions are used.

A method of quantitating RNA has also been suggested by Wang et al. (PNAS 86 (1989), 9717). This PCR is stopped in the exponential phase. By amplifying various standard concentrations, the authors provide a calibration curve (external standardisation). Since in the exponential reaction phase the number of PCR products, or increases directly proportional to the number of RNA molecules present, this calibration curve is a straight line in which one can finally read off the concentration of an amplified sample. A disadvantage of this method is that the final concentration of the PCR products is relatively low so that sensitive detection methods must be used for the detection. Wang et al. use radioactively labelled nucleotides.

Porcher et al. (BioTechnique 13 (1992), 106) succeeded in improving the detection of small amounts of PCR products by employing fluorescence-labelled primers and quantitating the PCR products with an automatic laser fluorescence DNA sequencer.

All these methods enable the determination of small amounts of homologous sequences, such as certain genes, viral DNA sections or mRNA. Hitherto it has, however, not been possible to find an exact method of determining contaminating heterogenous genomic DNA.

In WO 94/12669, a PCR method is suggested for the detection of contaminating DNA, in which repetitive sequences of the genome are amplified. With this method, DNA amounts of from 0.1 pg to 0.01 pg are said to be detectable. A suitable quantitation of the chromosomal DNA is, however, not possible with this method. There is disclosed neither the addition of a standard prior to the amplification reaction, nor a procedure by which the total chromosomal DNA originally contained in the sample can be recalculated from the amount of the amplified DNA. It is only mentioned that the repetitive sequences have to be present in a concentration of at least 1% in the genome of the organism contaminating the sample. However, in the determination of contaminating DNA of Hamster cells (CHO) described in the examples, it is not stated how many repetitive sequences are contained in the CHO genome. Also in the literature it was not possible to find any data in this respect. In principle, however, without these data, it is not possible to recalculate exactly the content of contaminating DNA in a sample, since for such a recalculation in any event a quantitative relationship between the amplified DNA piece and the entire chromosomal DNA is necessary.

Mention be also be made that according to WO 94/12669 the detection of the PCR products is effected with the dye Hoechst 32258, which deposits in DNA. This dye is added to the reaction products after the PCR. Despite the fact that this analytics precludes the use of an internal standard, this characterisation, because of its low sensitivity, is not suitable for an exact quantitation of DNA. Yet this was not the object of WO 94/12669. This method of detecting DNA was only intended to provide a yes/no answer to the question whether or not chromosomal DNA is contained in the sample to be examined.

Yet an exact DNA concentration determination by means of PCR necessitates the addition of an internal standard, since it has been shown that the efficiency of the PCR may often differ from reaction vessel to reaction vessel. This difference in efficiency may lead to differences in the results of up to $10^{5}$. With the method according to WO 94/12669, this source of error is completely ignored, and thus the reproducibility of the method according to WO 94/12669 is doubtful.

The present invention thus has as its object to provide a method of quantitating chromosomal DNA which allows for a very precise quantitative information regarding the total amount of chromosomal DNA present in a sample.

The method according to the invention and of the initially defined type is characterised in that
  prior to amplification in a manner known per se, a given amount of a known nucleic acid is added to the sample as an internal standard, wherein the standard nucleic acid differs from the genomic DNA to be quantitated in at least one detectable characteristic, and
  the amount of amplified genomic DNA and the amount of amplified standard nucleic acid are determined, and, departing from the amount of standard nucleic acid obtained, the amount of the genomic DNA originally present in the sample is determined.

By this method it is made possible for the first time to determine the content of chromosomal DNA present in a sample via quantitation of a certain partial amount of the chromosomal DNA (in the present case a certain repetitive sequence).

In principle, nucleic acid amplification means methods based on the technology developed by Mullis et al. (U.S. Pat. Nos. 4,683,195 and 4,683,202), and others, e.g. the polymerase chain reaction (PCR), the reverse transcriptase-PCR (RT-PCR) of the ligase-CR (LCR).

The standard nucleic acid must differ from the genomic DNA to be amplified in at least one detectable characteristic, yet it should be capable of being amplified by aid of the same primers. Standard nucleic acids having a size different from that of the genomic DNA to be amplified or having a restriction cleavage site different from that of the genomic DNA to be amplified have proved to be convenient. Preferably, the standard nucleic acid is a DNA, since the similarity between standard nucleic acid and the chromosomal DNA to be quantitated contained in the sample should be as high as possible. This also applies to GC content, restriction sites, sequence etc. Preferred standards differ from the chromosomal DNA to be amplified by 1% to 20% of their lengths. The exact sequence of the standard nucleic acid should, of course, be known.

The primers used in the amplification procedure preferably contain groups which increase the detection limit of the amplified nucleic acids, e.g., fluorescent or radioactive groups or chemical groups which can be detected by means of affine proteins and subsequent detection reactions (e.g., Biotin-Avidin, Digoxigenin labelling etc.), primers containing fluorescent groups being particularly preferred.

The preferred repetitive genomic sequence for the analysis of DNA are Alu-sequences or Alu-equivalent sequences, the primers preferably bind to a portion of the Alu-equivalent consensus sequences, in particular Alu-equivalent consensus sequences of mammals, in particular of rodents and primates.

The determination of the DNA amounts (basically, by DNA amount the quantity of DNA is to be understood; a DNA amount may, e.g., be given in the form of a mass (mg, $\mu$g, ng, pg, . . .) or as a number of copies of a certain DNA molecule) after the amplification may be effected in the most varying ways, in most cases, however, a step must be provided in which the amplified standard nucleic acid is separated from the amplified genomic DNA to be quantitated, and the separated DNA amounts are determined separately. Preferably, this separation step consists in a gel electrophoresis or in a chromatographic method.

Detection methods which take place automatically and which combine the separation and quantitation step have proved to be particularly suitable. A preferred embodiment of the method according to the invention thus consists in that the determination of the amounts of amplified nucleic acids is effected by using a nucleic acid detection device, preferably a fluorescence-sensitive nucleic acid detection device. Examples of such nucleic acid detection devices are automatic DNA sequencers with laser-induced fluorescence measuring devices (e.g. Gene Scanner®373A of Applied Biosystems) or HPLC-devices. With these devices it is possible to separate DNA molecules from each other, which differ in length merely by one base pair (bp).

A particular advantage of the Gene Scanner is that it is possible to differentiate between different fluorescence dyes in one single lane. This allows for the simultaneous processing of a plurality of samples on one gel, since all lanes available on the gel may be used for samples. Furthermore, it is possible to analyse a plurality of PCR products, labelled with different fluorescence dyes, in one single lane (multiplex-PCR), and thereby to detect genomic DNA of various origins in a sample. When simultaneously detecting two different nucleic acids, e.g., in one sample, furthermore expenditures and costs are nearly cut in half. When using the method according to the invention in a routine operation, this is of particular advantage. In contrast thereto, automatic laser fluorescence DNA sequencer used by Porcher et al. for analysing PCR products can analyse only one fluorescence dye (and thus only one DNA) per lane.

In a preferred embodiment of the method according to the invention, the amplification step is stopped already in the exponential phase.

Thereby the ratio of the number of copies of the amplified standard is directly proportional to the number of copies of the repetitive sequence. Furthermore, by co-amplification of a single standard, the number of copies of the repetitive sequence can be determined. In this respect the method according to the invention is by far superior to the frequently used method of Gilliland et al., since, per sample, only one standard need be run along, whereas the method according to Gilliland is the more precise, the more standards are used in different dilutions in different samples.

With the method according to the invention, preferably contaminating genomic DNA is determined. This determination is particularly important when determining the contaminating DNA in vaccines or in the quality control of recombinant products derived from cell cultures.

The amount of genomic DNA to be quantitated contained in the sample is preferably determined from the amount of amplified standard nucleic acid by means of a calibration curve.

So far, there have not been any references in the literature as to how a conclusion should be drawn from a previously determined smaller amount (number of copies of the repetitive sequences) to a larger, total amount (genomic DNA). It is merely known that the portion of the repetitive sequences in the genome is in the range of 1–10%. So far, a linear connection between an amplified repetitive sequence and the total amount of genomic DNA has not been disclosed.

Preferably, this connection is to be made by means of a calibration curve which can be found in the following manner:

Various known concentrations of a genomic DNA of a species are amplified with the method according to the invention in a competitive nucleic acid amplification method by using an internal standard. The method is stopped in the exponential phase, and the amounts of the amplified nucleic acids are determined.

The peak area (=number of copies) yielded by the amplified internal standard is then directly proportional to the peak area (=number of copies) of the amplified repetitive sequence of the genomic DNA utilized. To obtain the calibration curve, the number of copies of the repetitive sequence calculated therefrom are plotted against the originally utilized amount of genomic DNA. In this respect it has surprisingly been found that at low DNA concentrations (0 to 60 pg/ml), this calibration curve is a straight line. From this straight line, a factor can be calculated which is finally used for determining the unknown DNA amounts.

According to the method of the invention, thus the amount of genomic DNA is calculated in pg/ml according to the following formula:

$$m_{sample} = A_{sample}/A_{standard} \times N_{standard} \times F_1 \times D \times 1/F_2$$

wherein $A_{sample}$ is the peak area of the amplified chromosomal DNA of the sample, $A_{standard}$ is the peak area of the amplified internal standard, $N_{standard}$ are the employed copies of the internal standard, $F_1$ is the ratio of the volume of the standard to the extracted volume, D is the dilution factor (if the sample has been diluted prior to extraction), and $F_2$ is the conversion factor which indicates how many detectable copies of the repetitive sequence are contained per pg of genomic DNA.

This calibration curve is characteristic of the genomic DNA employed, the primers used and the specially selected amplification conditions.

Further criteria in the quantitation of chromosomal DNA are the sensitivity and the reproducibility. With the method according to the invention, DNA amounts in the range of 1 pg to 100 pg can be determined very precisely and reproducibly. Yet by this, the sensitivity limit of the method has not been reached by any means.

The method according to the invention is particularly suitable for the checking and the quality control of biotechnologically produced proteins, there being no restriction as to the production method of these proteins. For example, recombinant proteins, transgenic proteins or proteins recovered by means of hybridoma technology can be assayed for their content of chromosomal DNA with the method according to the invention. Multiplex analysis enables the assaying of monoclonal antibodies grown in hybridoma cell lines for contaminating DNA of the origin species in a simple and efficient manner.

Particularly in the case of vaccines or recombinant proteins, quality control is faced with background problems. Thus, when determining contaminating chromosomal DNA in primate cell cultures, also the impurities caused by handling during the production or processing of the products can be covered by the method according to the invention, if the primers employed are specific for all Alu-sequences of primates. If, however, the production of recombinant proteins is effected in cell cultures of non-primates, such as, e.g., CHO (Chinese hamster ovary cells), BHK (Baby hamster kidney cells), or CEC (chick embryo cells), the detection limit with the method of the invention is far lower, since the problem of impurities caused by handling of the sample is excluded. The quantitation methodics according to the invention is particularly preferably employed with genomic DNA of CHO—, Vero—(monkey cell line), BHK—, SK-Hep1—(human liver cell line), hybridoma cells or CEC cells, since these cell cultures are the most commonly used in the production of vaccines, recombinant proteins or monoclonal antibodies.

The reproducibility of the method according to the invention amounts to at least 95%. To obtain this, care must be taken that the efficiency of the amplification reaction for the standard and the sample is equal. The efficiency of the amplification reaction is primarily of importance if it is stopped in the exponential phase.

A further aspect of the present invention thus relates to the use of the method according to the invention for the checking and the quality control of biological preparations, in particular of biotechnologically produced preparations, since with these the danger of contamination with DNA is particularly high. Advantageously, the method of the invention is utilized in the checking and the quality control of HIV surface antigen gp160, recombinant blood factors, plasma proteins and vaccines (e.g. vaccines against herpes, influenza and tick-borne encephalitis (TBE) viruses).

On account of the high sensitivity and the particularly low detection limit of the method according to the invention, new quality criteria can be determined for biological products which are defined by an extremely low or absent content of contaminating nucleic acids.

According to a further aspect, the present invention thus relates to biological, in particular biotechnological, products which have a content of chromosomal DNA lying at least below the allowed limits of 10 or 100 pg per dose, measured with the present method, and thus may be deemed substantially free from foreign DNA.

Among the preferred products are viral proteins, such as gp160, recombinant blood factors, plasma proteins, as well as vaccines, particularly against herpes, influenza, hepatitis or TBE viruses.

The efficiency of the PCR is, e.g., influenced by the binding of the primers to standard and sample nucleic acids. For this reason, preferably the same primers are used for standard and sample, and these primers should possibly be 100% homologous to the primer binding sites of standard and genomic DNA to be amplified. For the synthetic standard, this is no problem, yet for the genomic sequences to be amplified this is a problem indeed. Repetitive sequences are not necessarily homologous by 100%, frequently they have different sequences. When selecting the primers, thus care must be taken that the most thoroughly conserved nucleotide sequence is used. The less homologous the primer to the genomic repetitive sequence, the poorer the binding of the primer, and the poorer also the efficiency of the PCR. In the method according to the invention the primers are chosen by alignment of conserved DNA sections within the repetitive sequences in gene data libraries.

Therefore, according to a further aspect the present invention relates to primers used in the present method, i.e.

Alu A2/2: GCCGGGCGTAGTGGCGGGCGCCTG-TAGT bp 149–176 Seq.ID 1

Alu B: GAGACAGAGTCTCGCTCTGTCGCCCAGG bp 294–267 Seq.ID 2 (numbering according to Batzer et al. (Nucl. Acid Res. 18 (1990) 6793)

CR1: ATGAGGCACTGGAACAGGTTGCCC bp 260–283 Seq.ID 3

CR1A CAGGGCCACATCCAGCCTGG bp 345–326 Seq.ID 4 numbering according to Stumph et al. (PNAS 81 (1984) 6667–6671)

and to plasmids for the production of the standards, i.e.

pAlu–wt (consisting of the known pCRII-plasmid and an insert in the multiple cloning site, which insert contains the base pairs (bp) 148 to 294 of the Alu-repeat-specific sequence from Batzer et al.)

pAlu20(derived from pAlu–wt with a deletion of 20 bp at bp 178 of the Alu-repeat-specific sequence from Batzer et al.)

pCR1–wt (consisting of the known pCRII-plasmid (of InVitrogen) and an insert at the EcoRI site of the pCRII-plasmid, which insert contains the bp 260 to 345 of the CR1 sequence from Stumph et al. (1984)

pCR1+11 (derived from the plasmid pCR1–wt, by making an insertion of 11 nucleotides at the bp 300 site).

pCR1–8 (derived from the plasmid pCR1–wt, by making a deletion of 8 nucleotides at position 302 (according to Stumph et al.).

The efficiency of the amplification reaction also depends on the type of the DNA molecule to be amplified. For the method of the invention, it has proved to be advantageous to add the internal standard in the linearised form prior to amplification. Thereby, further differences in the efficiency of the reaction are compensated, which go back to the different forms of the DNA to be amplified.

According to a further aspect, the present invention also relates to a kit for quantitating genomic nucleic acids in a sample comprising at least one known nucleic acid as internal standard differing from the nucleic acids to be quantitated in at least one detectable characteristic, fluorscence labelled primers binding to the standard nucleic acid and the nucleic acid to be quantitated, positive controls comprising known amounts of genomic nucleic acid, a negative control comprising buffer free of nucleic acids and a manual.

Preferred embodiments of the kit according to the present invention are as follows:

1. A kit for the quantitation of genomic primate DNA in a sample comprising
   as internal standard plasmid pAlu20
   fluorescence labelled primers Alu A2/2 and AluB
   positive controls comprising known amounts of Vero cell DNA
   a negative control comprising a buffer free of genomic nucleic acid and
   a manual.

2. A kit for the quantitation of genomic avian DNA in a sample comprising
   as internal standard plasmids pCR1+15 and pCR1−8
   fluorescence labelled primers CR1 and CR1A
   positive controls comprising known amounts of avian DNA
   a negative control comprising a buffer free of genomic nucleic acid and
   a manual.

The invention will be explained in more detail by way of the following examples and the associated drawing figures, to which, however, it shall not be limited. In particular, the drawings show that the method of the invention is excellently suited for a routine, quick, yet precise and reproducible quantitation of chromosomal DNA in the most varying samples.

BRIEF DESCRIPTION OF THE FIGURES

FIGS. 2-A to 2-I show the results of quantitation of chromosomal monkey-DNA; and FIGS. 3-A to 3-F show the results of the quantitation of chromosomal chicken-DNA;

EXAMPLES

Figure 1:
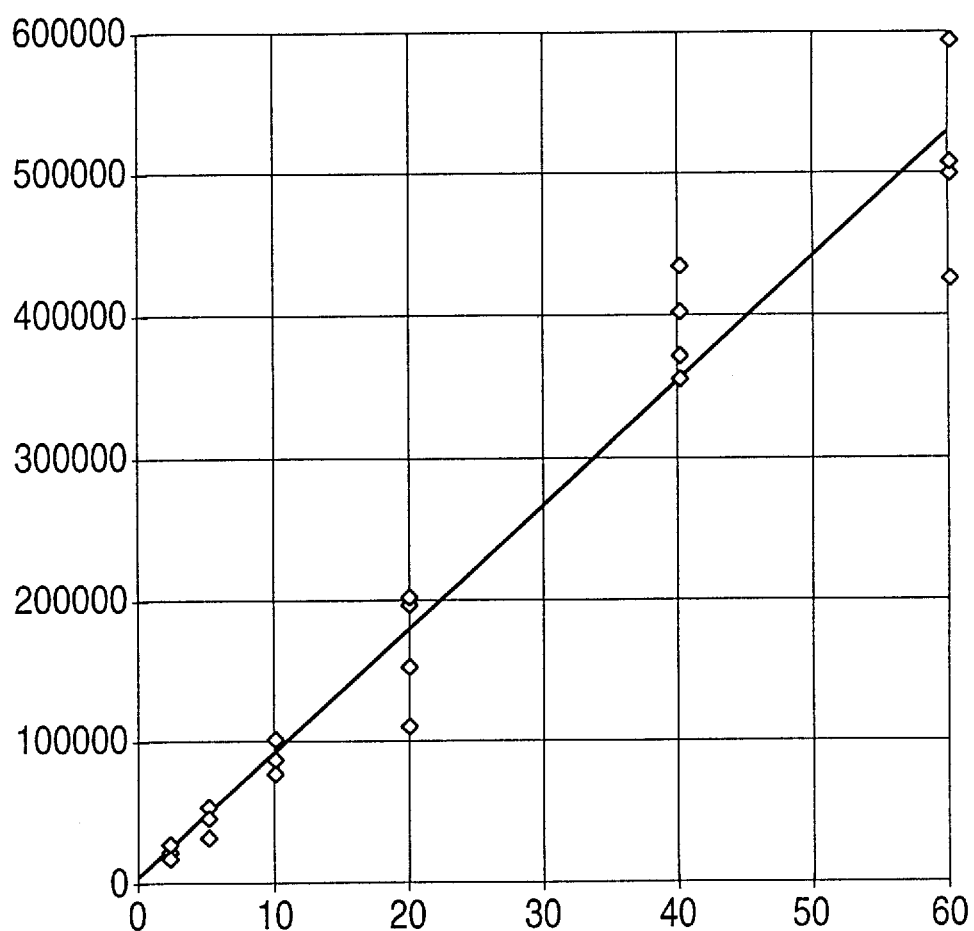
FIG. 1 shows the calibration straight line for chromosomal monkey DNA, wherein the amount of genomic DNA in pg/ml was plotted against the number of the copies found per ml.

1. General working instructions:

1.1 Principle of the method

Nucleic acids of the most varying origin are amplified by means of PCR by using primers containing fluorescent groups (Saiki et al., Science 239 (1985) 487–491). The analysis and the quantitation of the amplified PCR products obtained were effected by aid of an automatic DNA sequencer having a laser-induced fluorescence measuring means (373A Gene-Scanner® of Applied Biosystems). This instrument is capable of separating according to size the fluorescence-labelled PCR products by means of a gel electrophoresis in a polyacryl amide gel under denaturing conditions and to determine their amount quantitatively. The number of copies of certain sequences in the sample is determined on the basis of the intensities obtained of PCR products of chromosomal DNA and internal standard. By using a given ratio between the number of amplified repetitive chromosomal sequences per standard mass of DNA (cf. "Providing the calibration straight line"), it is possible to draw a direct conclusion to the entire chromosomal DNA present in the sample.

1.2. Extraction of the nucleic acids

To 500 μl of a sample 5 μl of 1M TRIS/HCl pH 8.0 and 10 μl of proteinase K (Boehringer Mannheim, 20 mg/ml) are added, as well as 20 μl of a 20% SDS. A certain amount of standard nucleic acid and 1 μg herring sperm DNA is added and the sample is incubated for 1 hour at 56° C. The sample is successively extracted with phenole and chloroform, and 10 μl of glycogen (Boehringer Mannheim, 20 mg/ml) are added. Subsequently, DNA is precipitated with ethanol, centrifuged, the pellet is washed and finally re-dissolved in water.

1.3. PCR

In a known manner, the PCR set-up contains an aliquot of the extracted nucleic acid, PCR buffer (Boehringer Mannheim), $MgCl_2$, dNTPs, primer, Taq-DNA-polymerase (Boehringer Mannheim, 5.0 U/μl) and water. The PCR is carried out according to the instructions of the producer of buffer and enzyme and according to common working instructions (Mullis et al., Methods in Enzymology 155 (1987), 335) in a PCR apparatus (GeneAmp System 9600 of Perkin-Elmer).

1.4. Analysis of the products

For determining and quantitating the PCR products, 0,5 to 1.0 μl are taken from the PCR solution and analysed according to the producer's instructions in a 373A instrument of Applied Biosystems and the special gene scan software.

2.1. Example 1: Quantitating genomic monkey-DNA

In this quantitation, primers are used which bind in a highly conserved region in the so-called "Alu repeat" sequences and amplify a 146 bp fragment (Jelinek et al., Ann. Rev. Biochem. 51 (1982) 813–844), i.e.

Alu A2/2: GCCGGGCGTAGTGGCGGGCGCCTG-TAGT bp 149–176 Seq.ID 1

Alu B: GAGACAGAGTCTCGCTCTGTCGCCCAGG bp 294–267 Seq.ID 2 (numbering according to Batzer et al.). The primers have been produced on a DNA synthesizer (Applied Biosystems 394 DNA Synthesizer) by using the phosphoamidite chemistry.

The standard plasmid pAlu20 is derived from the plasmid pAlu–wt, which consists of the known PCRII plasmid (of InVitrogen) and an insert at the multiple cloning site of the pCRII plasmid, which insert contains the bp 148 to 294 of the Alu-repeat-specific sequence from Batzer et al.

In pAlu20, the bp 178 to 197 were deleted. The plasmid was purified (QUIAGEN method), the concentration was determined by spectroscopical measurement at 260 nm, it was cleaved with EcoRI and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

The lengths of the PCR products of standard and wild-type DNA thus are 126 and 146 bp.

2.1: Providing the calibration curve with monkey DNA

To determine the number of Alu-copies per pg of genomic monkey DNA, 3 calibration runs were each carried out (blank, 2 pg, 5 pg, 10 pg, 20 pg, 40 pg, 60 pg, 100 pg DNA/ml). All the data obtained (6 PCR per concentration stage) are summarized in Table 1, and the regression straight line is illustrated in FIG. 1.

TABLE 1

| DNA | CF | RG | MV | SD | VC % |
|---|---|---|---|---|---|
| 0 | | 4533.92996 | | | |
| 2 | 21599.4238 | 21974.0922 | | | |
| 2 | 18983.3919 | 21974.0922 | 20099.8091 | 3822.30746 | 19.0166357 |
| 2 | 19900.3524 | 21974.0922 | | | |
| 2 | 25246.6524 | 21974.0922 | | | |
| 2 | 14769.225 | 21974.0922 | | | |
| 5 | 44883.8779 | 48134.3354 | | | |
| 5 | 52631.2571 | 48134.3354 | | | |
| 5 | 51109.4418 | 48134.3354 | 45055.9297 | 8108.004 | 17.9954205 |
| 5 | 32068.2966 | 48134.3354 | | | |
| 5 | 44586.7749 | 48134.3354 | | | |
| 10 | 97555.2485 | 91734.7409 | | | |
| 10 | 101015.717 | 91734.7409 | 90598.5793 | 10754.6015 | 11.8706073 |
| 10 | 86335.9144 | 91734.7409 | | | |
| 10 | 77487.4372 | 91734.7409 | | | |
| 20 | 108834.009 | 178935.552 | | | |
| 20 | 199305.642 | 178935.552 | | | |
| 20 | 203203.788 | 178935.552 | 172039.16 | 41076.2263 | 23.876091 |
| 20 | 197098.228 | 178935.552 | | | |
| 20 | 151754.131 | 178935.552 | | | |
| 40 | 363341.143 | 353337.174 | | | |
| 40 | 402578.42 | 353337.174 | | | |
| 40 | 433036.566 | 353337.174 | 383303.318 | 33743.5526 | 8.8033552 |
| 40 | 351420.48 | 353337.174 | | | |
| 40 | 366139.983 | 353337.174 | | | |
| 60 | 594815.223 | 527738.796 | | | |
| 60 | 505612.823 | 527738.796 | 506228.628 | 69570.4812 | 13.7428975 |
| 60 | 424808.212 | 527738.796 | | | |
| 60 | 499678.254 | 527738.796 | | | |

DNA: DNA in pg/ml
CF: copies found
RG: regression
MV: mean value
SD: standard deviation
VC: variation coefficient Calculation of the data was effected by means of the following relationships:

$$Area_{sample} : Area_{pAlu-20} = x$$

$$X - (Area_{blank}) : Area_{pAlu-20} = y \text{ (corrected area ratio)}$$

y multiplied by 100 000=number of copies in 500 µl sample=z (500 µl were extracted, 100 000 copies of the standard plasmid were added)

z multiplied by 2=number of copies per ml

After having calculated the regression straight line (y =4533.9+8720.1 x) there resulted an average value of 9200 copies per pg of genomic monkey DNA.

2.2. Quantitation of chromosomal monkey DNA (vero cells)

Pre-stages of vaccine batches produced according to Barrett et al. (AIDS Research and Human Retroviruses 5 (1989), 159–171) were assayed by means of DNA extraction and quantitative PCR with the help of the primers Alu A2/2 and AluB and an internal standard (pAlu20) which is recognized by the same primers, yet yields a differently sized PCR product. The results of the assays are illustrated in Table 2 and FIGS. 2-A to 2-I.

Table 2 lists the type, extent and measured values of the measured samples. In column 1, the number of copies of the standard plasmid pAlu20 is given; column 2 gives the dilution stage of the sample, wherein 1 is an undiluted sample; column 3 gives the extracted volume of the sample; columns 4 and 5 give the type of sample (batch number of the gp160 preparation; buffer d dilution of the standard); column 6 gives the measured values in pg of Vero total DNA per ml of sample, and column 7 gives the mean values of these measurements; column 8 gives the number of the lane in which the sample has been analysed (cf. also FIGS. 2-A to 2-I); columns 9 and 10 give the areas of the measured standard peaks and of the peak of chromosomal DNA to be measured. The first line is a control line.

TABLE 2

| | | | | | | | | | |
|---|---|---|---|---|---|---|---|---|---|
| 100000 | 5 | 0.5 | 311594 1:4 | A 1:5 (1) | 241 | 198.5 | 265, 01 | 12958 | 27170 |
| 100000 | 5 | 0.5 | 311594 1:4 | A 1:5 (1) | 166 | | 265, 02 | 12328 | 18096 |
| 100000 | 10 | 0.5 | 311594 1:4 | A 1:10 (2) | 187 | | 265, 03 | 11749 | 10007 |
| 100000 | 10 | 0.5 | 311594 1:4 | A 1:10 (2) | 200 | | 265, 04 | 14171 | 12641 |
| 100000 | 5 | 0.5 | 311594 | B 1:5 (3) | 429 | 430.5 | 265, 05 | 13484 | 40634 |
| 100000 | 5 | 0.5 | 311594 | B 1:5 (3) | 704 | | 265, 06 | 14788 | 88535 |
| 100000 | 10 | 0.5 | 311594 | B 1:10 (4) | 292 | | 265, 07 | 19993 | 25922 |
| 100000 | 10 | 0.5 | 311594 | B 1:10 (4) | 297 | | 265, 08 | 28919 | 38011 |
| 100000 | 5 | 0.5 | buffer PBS | C 1:5 (5) | 0 | <2 | 265, 09 | 29499 | 1931 |
| 100000 | 5 | 0.5 | buffer PBS | C 1:5 (5) | 2 | | 265, 10 | 30666 | 2641 |

TABLE 2-continued

| | | | | | | | | | |
|---|---|---|---|---|---|---|---|---|---|
| 100000 | 10 | 0.5 | buffer PBS | C 1:10 (6) | <2 | | 265, 11 | 18919 | 1824 |
| 100000 | 10 | 0.5 | buffer PBS | C 1:10 (6) | <2 | | 265, 12 | 19812 | 2072 |
| 100000 | 5 | 0.5 | 311594 | D 1:5 (7) | 621 | 572 | 265, 13 | 13639 | 72068 |
| 100000 | 5 | 0.5 | 311594 | D 1:5 (7) | 820 | | 265, 14 | 10835 | 73990 |
| 100000 | 10 | 0.5 | 311594 | D 1:10 (8) | 407 | | 265, 15 | 40842 | 72585 |
| 100000 | 10 | 0.5 | 311594 | D 1:10 (8) | 440 | | 265, 16 | 30240 | 57937 |
| 100000 | 5 | 0.5 | | TK E 1:5 (9) | −1 | 49.75 | 265, 17 | −1 | −1 |
| 100000 | 5 | 0.5 | | TK E 1:5 (9) | 16 | | 265, 18 | 36970 | 7232 |
| 100000 | 10 | 0.5 | | TK E 1:10 (10) | 17 | | 265, 19 | 45300 | 6402 |
| 100000 | 10 | 0.5 | | TK E 1:10 (10) | 168 | | 265, 20 | 30372 | 23499 |
| 100000 | 5 | 0.5 | 311594 | F 1:5 (11) | 393 | 408.25 | 265, 21 | 27779 | 93765 |
| 100000 | 5 | 0.5 | 311594 | F 1:5 (11) | 359 | | 265, 22 | 27093 | 03584 |
| 100000 | 10 | 0.5 | 311594 | F 1:10 (12) | 403 | | 265, 23 | 39560 | 09666 |
| 100000 | 10 | 0.5 | 311594 | F 1:10 (12) | 478 | | 265, 24 | 30846 | 64072 |
| 100000 | 1 | 0.5 | | H2O (13) | 0 | | 265, 25 | 61656 | −1 |
| 100000 | 1 | 0.5 | | H2O (13) | 0 | | 265, 26 | 47680 | −1 |
| 100000 | 1 | 0.5 | | H2O (14) | 0 | | 265, 27 | 24046 | 1739 |
| 100000 | 1 | 0.5 | | H2O (14) | 0 | | 265, 28 | 43898 | 2406 |
| 100000 | 1 | 0.5 | | H2O (15) | 0 | | 265, 29 | 47080 | 3223 |
| 100000 | 1 | 0.5 | | H2O (15) | 0 | | 265, 30 | 28895 | 1978 |
| 100000 | 1 | 0.5 | | 20pg DNA (16) | 22 | | 265, 31 | 47115 | 48181 |
| 100000 | 1 | 0.5 | | 20pg DNA (16) | 22 | | 265, 32 | 43086 | 44121 |
| 100000 | 1 | 0.5 | | 5pg | 4.3 | | 265, 33 | 11939 | 44607 |
| 100000 | 1 | 0.5 | | 5pg | 3.6 | | 265, 34 | 12691 | 39288 |
| 100000 | 1 | 0.5 | | POR | 0 | | 265, 35 | −1 | −1 |
| 100000 | 1 | 0.5 | | POR | 0 | | 265, 36 | −1 | −1 |

FIGS. 2-A to 2-I illustrate the graphic evaluation of the quantitative determination of the PCR products. The intensities of the fluorescence signals of the PCR products (and by-products) are illustrated in the various lanes. The products can be identified by way of their defined size (in bp). The standard pAlu20 (S) appears at 126 bp, the wild-type peak (P) at 146 bp. Peak areas and calculation of the DNA amount are given in Table 2.

3.1. Quantitation of chromosomal chicken DNA

The idea of this optimizing of primers and PCR conditions is the precise and specific measurement in the concentration range 1 pg–100 pg of chicken DNA per ml sample. To obtain the desired specificity and a sensitivity of the measurement in the pg region, the sequence of a repetitive DNA family was chosen as target sequence for the PCR. These DNA families are not only species-specific to a great extent, but also occur in a great number of copies in the genome and thus meet the criteria for a determination of small amounts of specific DNA. In the family of aves (birds), the CR1-repetitive DNA family has been described which is said to be present in 7000 to 20000 copies per genome (Stumpf et al., Nucleic Acids Res. 9 (1981) 5383–5397). A comparison between various members of this family shows a highly conserved region at the site 261 to 391 (according to the numbering of Stumpf et al. 1984). The primer pair for determining the chicken DNA was chosen by alignment of the repetitive sequences such that it binds specifically within this conserved sequence and amplifies a DNA fragment having a length of 846 bp, i.e.

CR1: ATGAGGCACTGGAACAGGTTGCCC bp 260–283 Seq. ID 3

CR1A CAGGGCCACATCCAGCCTGG bp 345–326 Seq. ID 4 (numbering according to Stumpf et al. (1984)). The primers were produced on a DNA synthesizer (Applied Biosystems 394 DNA synthesizer) by using the phosphoamidite chemistry.

Standard plasmids pCR1+11 and pCR1-8 were obtained by inserting inbetween the NcoI and SacI sites of the pBluescript vector, synthetic oligonucleotides containing CR1 derived sequence from position 260 to 345 (according to Stumpf at al.). For pCR1+11, the CR1 sequence contains an insertion of 11 nucleotides and for the standard plasmid pCR1-8 a deletion of 8 nucleotides at position 302 (according to Stumph et al.). Therefore, the PCR products derived from these standard plasmids are 95 bp and 76 bp in length. The plasmid was purified (QUIAGEN-method), the concentration was determined by spectroscopic measurement at 260 nm, it was cleaved with EcoRI and diluted in a 10 mM TRIS/HCl pH 8/0.1 mM EDTA buffer (Sambrook et al., Molecular Cloning, Second Edition, Cold Spring Harbor Lab Press, Cold Spring Harbor (1989)).

The calibration straight line was provided analogous to 2.1. In the experiment, 200, 40, 20, 10, 4 and 2 pg of genomic DNA were extracted from chicken cells (CEF-cells) and subjected to PCR with the fluorescence-labelled primers CR1 and CR1A. As the specificity control, 100 pg of mouse and human chromosomal DNA were also subjected to PCR. 10 μl of water served as negative control.

The results of the assays are illustrated in Table 3 and in FIGS. 3-A to 3-F.

Table 3 gives the type, extent and measured values of the measured samples. In column 1 the number of the measurement (corresponds to one lane number in FIG. 3) is given; column 2 gives the utilized amount of genomic DNA of CEF cells; column 3 gives the area of the measured peaks.

TABLE 3

| 1 | CEF 200 pg/ml | 61192 |
|---|---|---|
| 2 | CEF 200 pg/ml | 77128 |
| 3 | CEF 40 pg/ml | 36856 |
| 4 | CEF 40 pg/ml | 29229 |
| 5 | CEF20 pg/ml | 22035 |
| 6 | CEF20 pg/ml | 19008 |
| 7 | CEF 10 pg/ml | 13658 |
| 8 | CEF 10 pg/ml | 11333 |
| 9 | CEF 4 pg/ml | 2958 |
| 10 | CEF 4 pg/ml | 6533 |
| 11 | CEF 2 pg/ml | 3471 |
| 12 | CEF 2 pg/ml | 2907 |
| 13 | H2O | 0 |
| 14 | H2O | 0 |
| 16 | Human DNA 100 pg/ml | 0 |
| 17 | mouse DNA 100 pg/ml | 0 |

In FIGS. 3-A to 3-F, the graphic evaluation of the determination of the PCR products is depicted. The intensities of the fluorescence signals of the PCR products (and by-products) are illustrated in the various lanes. The products can be identified by way of their defined size (in bp). The wild-type peak occurs at 86 bp, the peak areas are illustrated in Table 3.

In all the lanes in which chicken DNA was used, a defined peak occurred at 84 bp. In contrast thereto, no significant amount of 84 bp-specific product was detected, even if large amounts of human or mouse DNA-respectively, were used. On the basis of these results, the detection limit of chromosomal chicken DNA can be determined to be less than 2 pg/ml in the method according to the invention.

3.2. Quantitation of chicken DNA

Dilutions of chicken DNA of 25, 10, 5, 2.5 and 1 pg/ml and water were extracted and submitted to PCR. Table 4 gives the number of standard plasmid pCR+11 and plasmid pCR1-8 added (columns 1 and 2), the dilution (column 3), volume (column 4), sample description (column 5), comment (column 6), the number of CR1 sequences in the sample calculated with the -standard (column 7) or with the +standard (column 8), the mean value in pg of chicken DNA (column 9), the lane in which the sample has been analysed (column 10), and the peak areas of the -standard (column 11), the wild-type (column 12), and the +standard (column 13). The graphic evaluation of the determination of the PCR products is depicted in FIG. 3-E. The PCR products can be identified by their size. The wild-type peak occurs at 84 bp, the minus-standard peak at 76 bp and the plus-standard at 95 bp, the peak areas of the fluorescence signals are given in Table 4.

TABLE 4

| N- added | N+ added | Dilution | Volume | Sample | Comment | N- Base | N+ Base | Result | GS#, Lane | A- | Awl | A+ |
|---|---|---|---|---|---|---|---|---|---|---|---|---|
| 5000 | 15000 | 1 | 0.25 | 25 pg/ml | chick 32 | 113964 | 154065 | 26,8029 | chick 32, 13 | 2916 | 16616 | 6471 |
| 5000 | 15000 | 1 | 0.25 | 10 pg/ml | chick 32 | 51650 | 54126 | 10,5776 | chick 32, 14 | 4132 | 10671 | 11829 |
| 5000 | 15000 | 1 | 0.25 | 5 pg/ml | chick 32 | 22445 | 29066 | 5,1511 | chick 32, 15 | 3705 | 4158 | 8583 |
| 5000 | 15000 | 1 | 0.25 | 2.5 pg/ml | chick 32 | 13426 | 15697 | 2,9123 | chick 32, 16 | 4342 | 2915 | 11142 |
| 5000 | 15000 | 1 | 0.25 | 1 pg/ml | chick 32 | 6536 | 8486 | 1,5022 | chick 32, 17 | 4461 | 1458 | 10308 |
| 5000 | 15000 | 1 | 0.25 | 0 pg/ml | chick 32 | -1 | -1 | 0 | chick 32, 18 | 3560 | -1 | 9059 |

What we claim is:

1. A method for quantitating total heterogenous genomic DNA in a sample, said genomic DNA comprising repetitive sequences, comprising:
   adding to said sample a given amount of at least one nucleic acid as an internal standard, said at least one standard nucleic acid differing from said repetitive sequences in at least one detectable characteristic,
   amplifying said repetitive sequences and said at least one standard nucleic acid with a nucleic acid amplification process employing primers complementary to said repetitive sequences, and
   determining, as a first amount, the amount of amplified repetitive sequences, and, as at least one second amount, the amount of the at least one amplified standard nucleic acid, and
   determining from said first amount and said at least one second amount, as a third amount, the amount of total heteroqenous genomic DNA originally contained in said sample.

2. A method according to claim 1, wherein said primers contain a detectable group selected from the group consisting of fluorescent groups, radioactive groups and chemical groups detectable by affinity proteins and subsequent detection reactions.

3. A method according to claim 1, wherein said primers contain a fluorescent group.

4. A method according to claim 1, wherein said primers bind to repetitive Alu sequences or to repetitive Alu-like sequences.

5. A method according to claim 1, wherein said amplification process is allowed to reach the exponential phase before said first or second amounts are determined.

6. A method according to claim 1, wherein said at least one second amount is determined by using a nucleic acid detection device.

7. A method according to claim 3, wherein said nucleic acid detection device is a fluorescence-sensitive nucleic acid detection device.

8. A method according to claim 1, wherein said genomic DNA to be quantitated is a contaminating genomic DNA.

9. A method according to claim 1, wherein said primers are complementary to a part of an Alu-equivalent consensus sequence.

10. A method according to claim 8, wherein said genomic DNA to be quantified is a genomic DNA selected from the group consisting of CHO, Vero, BHK, SK-Hep 1, hybridoma and CEC cells.

11. A biological product substantially free of foreign heteroqenous genomic DNA, said qenomic DNA comprising repetitive sequences, as determined by a method of quantitating heteroqenous genomic DNA in a sample comprising:
   adding to a sample comprising the product a given amount of at least one nucleic acid as an internal standard, said at least one standard nucleic acid differing from said repetitive sequences in at least one detectable characteristic,
   amplifying said repetitive sequences and said at least one standard nucleic acid with a nucleic acid amplification process employing primers complementary to said repetitive sequences, and
   determining, as a first amount, the amount of amplified repetitive sequences, and, as at least one second amount, the amount of the at least one amplified standard nucleic acid, and
   determining from said first amount and said at least one second amount, as a third amount, the amount of total heteroqenous genomic DNA originally contained in said sample,
   wherein said biological product is substantially free from foreign heteroqenous genomic DNA if said third amount is less than 10 to 100 pg per dose.

12. A biological product according to claim 11, selected from the group consisting of viral proteins, recombinant blood factors, plasma proteins, vaccines, and monoclonal antibodies.

13. A primer comprising a sequence selected from the group consisting of SEQ ID NOS: 1, 2, 3 and 4.

14. A plasmid selected from the group consisting of pAlu-wt, pAlu-20, pCR1-wt, pCR1+11, and pCR1-8.

15. A kit for quantitating genomic nucleic acids in a sample comprising;

at least one known nucleic acid which differs from the nucleic acids to be quantitated in at least one detectable characteristic, as an internal standard, fluorescence-labelled primers binding to repetitive genomic sequences, a positive control comprising a known amount of genomic nucleic acid, and a negative control comprising a buffer free of nucleic acids.

16. A kit for the quantitation of genomic primate DNA in a samples, comprising:

as an internal standard, plasmid pAlu20 fluorescence-labelled primers Alu A2/2 and AluB a positive control comprising a known amount of Vero cell DNA and a negative control comprising a buffer free of genomic nucleic acid.

17. A kit for the quantitation of genomic avian DNA in a sample, comprising:

as an internal standard, plasmids pCR1+15 and pCR1-8 fluorescence-labelled primers CR1 and CR1A a positive control comprising a known amount of avian DNA and a negative control comprising a buffer free of genomic nucleic acid.

18. The method according to claim 9, wherein said primers are complementary to a vertebrate Alu-equivalent consensus sequence selected from the group consisting of rodent and primate consensus sequences.

19. The method according to claim 1, wherein said sample comprises a biological product selected from the group consisting of viral proteins, recombinant blood factors, plasma proteins, vaccines and monoclonal antibodies.

20. The method according to claim 1, wherein said at least one standard nucleic acid is plasmid pAlu20 and wherein said primers are fluorescence-labelled Alu A2/2 and fluorescence-labelled AluB.

21. The method according to claim 1, wherein said at least one standard nucleic acid is plasmids pCR1+15 and pCR1-8 and wherein said primers are fluorescence-labelled CR1 and fluorescence-labelled CR1A.

22. A method according to claim 1, wherein the amount of total heterogenous genomic DNA originally contained in said sample is determined by comparing said first amount to said at least one second amount using a conversion factor, wherein said conversion factor reflects the number of detectable copies of said repetitive sequences per pg of said genomic DNA.

23. A method according to claim 11, wherein the amount of total heterogenous genomic DNA originally contained in said sample is determined by comparing said first amount to said at least one second amount using a conversion factor, wherein said conversion factor reflects the number of detectable copies of said repetitive sequences per pg of said genomic DNA.

* * * * *